(12) United States Patent
Kim et al.

(10) Patent No.: US 11,953,504 B2
(45) Date of Patent: Apr. 9, 2024

(54) ANTIBODY SPECIFICALLY BINDING TO BOVINE PREGNANCY-ASSOCIATED GLYCOPROTEIN 1 AND USE THEREOF

(71) Applicant: SLSBIO CO., LTD., Gyeonggi-do (KR)

(72) Inventors: Bong Hui Kim, Gyeonggi-do (KR); Young Ju Ha, Chungcheongnam-do (KR); Se Young Kim, Gyeonggi-do (KR); Ji Na Kim, Gyeonggi-do (KR)

(73) Assignee: SLSBIO CO., LTD. (KR)

( * ) Notice: Subject to any disclaimer, the term of this patent is extended or adjusted under 35 U.S.C. 154(b) by 923 days.

(21) Appl. No.: 16/875,120

(22) Filed: May 15, 2020

(65) Prior Publication Data

US 2020/0326347 A1 Oct. 15, 2020

Related U.S. Application Data

(63) Continuation of application No. PCT/KR2018/013572, filed on Nov. 8, 2018.

(30) Foreign Application Priority Data

Nov. 15, 2017 (KR) .................. 10-2017-0152257

(51) Int. Cl.
G01N 33/68 (2006.01)
C07K 16/18 (2006.01)
C12N 5/12 (2006.01)

(52) U.S. Cl.
CPC .......... *G01N 33/689* (2013.01); *C07K 16/18* (2013.01); *C12N 5/12* (2013.01)

(58) Field of Classification Search
None
See application file for complete search history.

(56) References Cited

U.S. PATENT DOCUMENTS 7,687,281 B2    3/2010  Roth et al.
8,431,349 B2 *  4/2013  Mathialagan ...... G01N 33/6803
                                                    435/7.1

FOREIGN PATENT DOCUMENTS

CA          3082923 A1 *  5/2019  ............ C07K 16/18
KR    10-2013-0000950      1/2013
WO         2003/043524     5/2003

OTHER PUBLICATIONS

Harlow et al., Antibodies, A Laboratory Manual, Cold Spring Harbor laboratory, 1988, pp. 25-26 and 37-59 (Year: 1988).*
Edwards et al., "The remarkable flexibility of the human antibody repertoire; isolation of over one thousand different antibodies to a single protein, BLyS" J. Mol. Biol. (2003) 334, 103-118, DOI: 10.1016/j.jmb.2003.09.054 (Year: 2003).*
Lloyd et al., "Modelling the human immune response: performance of a 10e11 human antibody repertoire against a broad panel of therapeutically relevant antigens", Protein Engineering, Design and Selection, vol. 22, Issue 3, Mar. 1, 2009, pp. 159-168, https://doi.org/10.1093/protein/gzn058 (Year: 2009).*
Meyer et al., "New Insights in Type I and II CD20 Antibody Mechanisms-of-Action With a Panel of Novel CD20 Antibodies", British Journal of Haematology, 2018, 180, 808-820, |https://doi.org/10.1111/bjh.15132 (Year: 2018).*
Vajdos et al., "Comprehensive functional maps of the antigen-binding site of an anti-ErbB2 antibody obtained with shotgun scanning mutagenesis" J Mol Biol. Jul. 5, 2002;320(2):415-28, DOI: 10.1016/S0022-2836(02)00264-4 (Year: 2002).*
Szenci et al., Comparison of ultrasonography, bovine pregnancy-specific protein B, and bovine pregnancy-associated glycoprotein 1 tests for pregnancy detection in diary cows, Theriogenology, 50, (1998), p. 77-88. (Year: 1998).*
Zoli, et al., Radioimmunoassay of a bovine pregnancy-associated glycoprotein in serum: its application for pregnancy diagnosis, Biology of Reproduction, 1992, pp. 83-92, vol. 46 (1).
NCBI Reference Sequence XP_019810031.1, Predicted: pregnancy-associated glycoprotein 1 [Bos indicus], NCBI, Jan. 12, 2017. (1 page).
International Search Report for International Application PCT/KR2018/013572, dated May 20, 2019. (10 pages).

* cited by examiner

*Primary Examiner* — Ellen J Marcsisin
(74) *Attorney, Agent, or Firm* — Renaissance IP Law Group LLP

(57) ABSTRACT

The present disclosure relates to an antibody specifically binding to bovine pregnancy-associated glycoprotein 1 (bPAG1) or an antigen-binding fragment thereof. The present disclosure further relates to a hybridoma cell producing the antibody; a composition including the antibody as an effective ingredient for diagnosis of bovine pregnancy; and a kit for diagnosis of bovine pregnancy. The present disclosure also relates to a method of diagnosing bovine pregnancy. Binding specifically to bPAG1, which is a pregnancy-associated plasma protein in bovines, the antibody allows a simple diagnosis of pregnancy in animals such as bovines of which the reproduction is important, so that the antibody may be usefully applied in the livestock industry by increasing reproduction efficiency.

6 Claims, 7 Drawing Sheets

Specification includes a Sequence Listing.

FIG. 1

>sp | Q29432 | PAG1_BOVIN Pregnancy-associated glycoprotein 1 OS=Bos taurus PE=1 SV=1
MKWLVLLGLVAFSECIVKIPLRRLKTMRNVVSGKNMLNNFLKEHAYSLS
QISFRGSNLTT
HPLRNIKDLVYMGNITIGTPPQEFQVVFDTASSDLWVPSDFC(100)**TSPA
CSTHVRFRHLQSSTFRLTNKTFRITYGSGRMKGVVV**HDTVRIGNLVSTD
QPFGLSIEEYGFEGRIYDGVLGLNY
PNISFSGAIPIFDKLKNQRAISEPVFAFYLSKDEREGSVVMFGGVDHRYY
EGELNWVPLI
QAGDWSVHMDRISIERKIIACSDGCKALVDTGTSDIVGPRRLVNNIHRLIG
AIPRGSEHY
VPC(300)SEVNTLPSIVFTINGINYPVPGRAYILKDDRGRCYTTFQENRVS
SSTETWYLGDVFL RLYFSVFDRGNDRIGLARAV

```
                       SEQUENCE LISTING

<160> NUMBER OF SEQ ID NOS: 7

<210> SEQ ID NO 1
    <211> LENGTH: 20
    <212> TYPE: PRT
    <213> ORGANISM: Artificial Sequence
    <220> FEATURE:
    <223> OTHER INFORMATION: epitope of bPAG1

<400> SEQUENCE: 1

Ala Ser Ser Asp Leu Trp Val Pro Ser Asp Phe Cys Thr Ser Pro Ala
    1               5                   10                  15

Cys Ser Thr His
                20

<210> SEQ ID NO 2
    <211> LENGTH: 21
    <212> TYPE: PRT
    <213> ORGANISM: Artificial Sequence
    <220> FEATURE:
    <223> OTHER INFORMATION: epitope of bPAG1

<400> SEQUENCE: 2

Cys Val Arg Phe Arg His Leu Gln Ser Ser Thr Phe Arg Leu Thr Asn
    1               5                   10                  15

Lys Thr Phe Arg Ile
                20

<210> SEQ ID NO 3
    <211> LENGTH: 20
    <212> TYPE: PRT
    <213> ORGANISM: Artificial Sequence
    <220> FEATURE:
    <223> OTHER INFORMATION: epitope of bPAG1

<400> SEQUENCE: 3

Gly Ala Ile Pro Arg Gly Ser Glu His Tyr Val Pro Cys Ser Glu Val
    1               5                   10                  15

Asn Thr Leu Pro
                20

<210> SEQ ID NO 4
    <211> LENGTH: 21
    <212> TYPE: PRT
    <213> ORGANISM: Artificial Sequence
    <220> FEATURE:
    <223> OTHER INFORMATION: epitope of bPAG1
```

<400> SEQUENCE: 4

Cys Ser Ile Val Phe Thr Ile Asn Gly Ile Asn Tyr Pro Val Pro Gly
1               5                   10                  15

Arg Ala Tyr Ile Leu
            20

<210> SEQ ID NO 5
<211> LENGTH: 40
<212> TYPE: PRT
<213> ORGANISM: Artificial Sequence
<220> FEATURE:
<223> OTHER INFORMATION: bPAG1_100

<400> SEQUENCE: 5

Thr Ser Pro Ala Cys Ser Thr His Val Arg Phe Arg His Leu Gln Ser
1               5                   10                  15

Ser Thr Phe Arg Leu Thr Asn Lys Thr Phe Arg Ile Thr Tyr Gly Ser
            20                  25                  30

Gly Arg Met Lys Gly Val Val Val
            35                  40

<210> SEQ ID NO 6
<211> LENGTH: 40
<212> TYPE: PRT
<213> ORGANISM: Artificial Sequence
<220> FEATURE:
<223> OTHER INFORMATION: bPAG1_300

<400> SEQUENCE: 6

Ser Glu Val Asn Thr Leu Pro Ser Ile Val Phe Thr Ile Asn Gly Ile
1               5                   10                  15

Asn Tyr Pro Val Pro Gly Arg Ala Tyr Ile Leu Lys Asp Asp Arg Gly
            20                  25                  30

Arg Cys Tyr Thr Thr Phe Gln Glu
            35                  40

<210> SEQ ID NO 7
<211> LENGTH: 380
<212> TYPE: PRT
<213> ORGANISM: Artificial Sequence
<220> FEATURE:
<223> OTHER INFORMATION: PAG1_BOVIN Pregnancy-associated glycoprotein 1

<400> SEQUENCE: 7

Met Lys Trp Leu Val Leu Leu Gly Leu Val Ala Phe Ser Glu Cys Ile
1               5                   10                  15

Val Lys Ile Pro Leu Arg Arg Leu Lys Thr Met Arg Asn Val Val Ser
            20                  25                  30

Gly Lys Asn Met Leu Asn Asn Phe Leu Lys Glu His Ala Tyr Ser Leu
            35                  40                  45

Ser Gln Ile Ser Phe Arg Gly Ser Asn Leu Thr Thr His Pro Leu Arg
        50                  55                  60

Asn Ile Lys Asp Leu Val Tyr Met Gly Asn Ile Thr Ile Gly Thr Pro
65                  70                  75                  80

Pro Gln Glu Phe Gln Val Val Phe Asp Thr Ala Ser Ser Asp Leu Trp
                85                  90                  95

Val Pro Ser Asp Phe Cys Thr Ser Pro Ala Cys Ser Thr His Val Arg
            100                 105                 110

Phe Arg His Leu Gln Ser Ser Thr Phe Arg Leu Thr Asn Lys Thr Phe

-continued

```
            115                 120                 125
Arg Ile Thr Tyr Gly Ser Gly Arg Met Lys Gly Val Val His Asp
        130                 135                 140
Thr Val Arg Ile Gly Asn Leu Val Ser Thr Asp Gln Pro Phe Gly Leu
145                 150                 155                 160
Ser Ile Glu Glu Tyr Gly Phe Glu Gly Arg Ile Tyr Asp Gly Val Leu
                165                 170                 175
Gly Leu Asn Tyr Pro Asn Ile Ser Phe Ser Gly Ala Ile Pro Ile Phe
            180                 185                 190
Asp Lys Leu Lys Asn Gln Arg Ala Ile Ser Glu Pro Val Phe Ala Phe
        195                 200                 205
Tyr Leu Ser Lys Asp Glu Arg Glu Gly Ser Val Val Met Phe Gly Gly
    210                 215                 220
Val Asp His Arg Tyr Tyr Glu Gly Glu Leu Asn Trp Val Pro Leu Ile
225                 230                 235                 240
Gln Ala Gly Asp Trp Ser Val His Met Asp Arg Ile Ser Ile Glu Arg
                245                 250                 255
Lys Ile Ile Ala Cys Ser Asp Gly Cys Lys Ala Leu Val Asp Thr Gly
            260                 265                 270
Thr Ser Asp Ile Val Gly Pro Arg Arg Leu Val Asn Asn Ile His Arg
        275                 280                 285
Leu Ile Gly Ala Ile Pro Arg Gly Ser Glu His Tyr Val Pro Cys Ser
    290                 295                 300
Glu Val Asn Thr Leu Pro Ser Ile Val Phe Thr Ile Asn Gly Ile Asn
305                 310                 315                 320
Tyr Pro Val Pro Gly Arg Ala Tyr Ile Leu Lys Asp Asp Arg Gly Arg
                325                 330                 335
Cys Tyr Thr Thr Phe Gln Glu Asn Arg Val Ser Ser Ser Thr Glu Thr
            340                 345                 350
Trp Tyr Leu Gly Asp Val Phe Leu Arg Leu Tyr Phe Ser Val Phe Asp
        355                 360                 365
Arg Gly Asn Asp Arg Ile Gly Leu Ala Arg Ala Val
370                 375                 380
```

ANTIBODY SPECIFICALLY BINDING TO BOVINE PREGNANCY-ASSOCIATED GLYCOPROTEIN 1 AND USE THEREOF

CROSS-REFERENCE TO RELATED APPLICATIONS

This application is a continuation of PCT Application No. PCT/KR2018/013572, filed Nov. 8, 2018, which claims the benefit of priority to Korean Patent Application No. 10-2017-0152257, filed on Nov. 15, 2017, in the Korean Intellectual Property Office, the disclosures of which are incorporated by reference herein in their entireties.

TECHNICAL FIELD

The present disclosure relates to an antibody specifically binding to bovine pregnancy-associated glycoprotein 1 (bPAG1) and an antigen-binding fragment thereof.

REFERENCE TO SEQUENCE LISTING

Incorporated herein by reference in its entirety is a Sequence Listing in electronic format filed via EFS-Web on May 15, 2020, entitled "0527-000003USNPA_Sequence.txt," created on Nov. 15, 2017 and being 5,000 bytes in size.

BACKGROUND

In breeding of bovines that are industrial animals, income of farm households is achieved through production of calves in most cases. Fertilization is important in breeding of bovines, but early diagnosis of pregnancy of fertilized bovines also helps to separately manage non-fertilized bovines early so that the period of non-pregnant condition can be shortened, thereby reducing the cost of farming. Currently, diagnosis of bovine pregnancy is mostly performed by a veterinarian or an insemination technician according to a slipping method between 30 days and 42 days of pregnancy.

In addition, other diagnosis methods include testing progesterone in milk by radioimmunoassay (RIA). In this method, considering that progesterone is a steroid hormone required for the normal progression and maintenance of pregnancy, serum titers of progesterone increase in an early stage of pregnancy, and in this regard, the increased level of the hormone can be confirmed in milk. However, there are problems in that RIA not only has the risk of using radioactive materials, but also requires use of complicated experimental equipment, and since the amount of progesterone varies depending on a bovine, the criteria is unclear so that at least two rounds of the experiment need to be performed for accurate diagnosis. Therefore, there is a need to develop a new method of solving the existing problems, and at same time, diagnosing bovine pregnancy early in an easier and faster manner.

SUMMARY

Provided is an antibody specifically binding to bovine pregnancy-associated glycoprotein 1 (bPAG1) or an antigen-binding fragment thereof.

Provided is a hybridoma cell (Accession No: KCLRF-BP-00416) producing the antibody specifically binding to bPAG1 or the antigen-binding fragment thereof.

Provided is a composition including the antibody specifically binding to bPAG1 or the antigen-binding fragment thereof.

Provided is a kit including the composition for diagnosis of bovine pregnancy.

Provided is a method of diagnosing bovine pregnancy, the method including: contacting a sample with the antibody specifically binding to bPAG1 or the antigen-binding fragment thereof; and detecting bPAG1 bound by the antibody or the antigen-binding fragment thereof.

The present inventors prepared a hybridoma cell producing a novel monoclonal antibody that specifically binds to bovine pregnancy-associated glycoprotein 1 (bPAG1) which is a bovine gestational plasma protein, and separated and purified the antibody in large quantities to confirm whether a bovine is pregnant by a relatively simple method, thereby completing the present disclosure.

In the present specification, the term "bovine pregnancy-associated glycoprotein 1 (bPAG1)" as used herein is a bovine gestational plasma protein, and collectively refers to a blood stream that appears or increases depending on pregnancy. The bPAG1 may include a natural protein form, a variant thereof, and a functional equivalent thereof. The bPAG1 may be separated from a natural cell or a recombinant cell, or may be artificially synthesized.

In the present specification, the term "antibody" as used herein refers to an antibody that specifically binds to a single antigenic site. Unless otherwise specified, the antibody may be a molecule including an antigen-binding site that is formed by heavy and light chain polypeptides known in the art, or may be an antigen-binding fragment of the antibody. The antibody may be produced by a plasma cell or a hybridoma cell. The antibody may be a monoclonal antibody. In detail, the antibody may be a monoclonal antibody specifically binding to the bPAG1 that is produced by a hybridoma cell with Accession No: KCLRF-BP-00416. In the present specification, the term "antigen-antibody complex" as used herein refers to a combination of the bPAG1 and an antibody recognizing the bPAG1. The complex may be used to detect the bPAG1. The complex may be used, for example, to detect the bPAG1 in a biological sample, such as bovine urine, bovine serum, or bovine plasma.

According to an aspect of the present disclosure, provided is an antibody specifically binding to the bPAG1 or an antigen-binding fragment thereof. In detail, the antibody according to an embodiment of the present disclosure may include an antigen-binding fragment, as long as the antibody is capable of selectively recognizing the bPAG1, which is a bovine gestational plasma protein. The antigen-binding fragment may include a F(ab')2 fragment, a Fab fragment, a Fab fragment, a Fv fragment, and the like.

In one embodiment, as a result of analyzing an epitope that is specifically bound by a monoclonal antibody against the bPAG1, it was confirmed that the amount of the antibody specifically binding to the antigen increased depending on the concentration of the antigen. In particular, at the same antigen concentration, the amount of an antibody specifically binding to a polypeptide having an amino acid sequence of SEQ ID NO: 1 was significantly higher than the amount of an antibody specifically binding to a polypeptide having an amino acid sequence of one of SEQ ID NOs: 2 to 4. Accordingly, the antibody specifically binding to the bPAG1 may bind to an epitope polypeptide having an amino acid sequence of SEQ ID NO: 1. In addition, the complete form of the antibody has a structure including two full-length light chains and two full-length heavy chains, and each light chain may be connected to each heavy chain via a disulfide bond. The heavy chains may each include both a full-length heavy chain and a fragment thereof, the full-length heavy chain including: a variable region domain (VH) having an amino acid sequence including a sufficient variable region sequence to confer antigen specificity; and three constant region domains (CH1, CH2, and CH3). The light chains may each include both a full-length light chain and a fragment thereof, the full-length light chain including: a variable region domain (VL) having an amino acid sequence including a sufficient variable region sequence to confer antigen specificity; and a constant region domain (CL). Here, the constant regions of the heavy chain may have gamma (γ), mu (μ), alpha (α), delta (δ), and epsilon (ε) types, and the constant region of the light chain may include kappa (κ) and lambda (λ) types. Here, the antibody may be immunoglobulin M (IgM).

According to another aspect of the present disclosure, provided is a hybridoma cell (Accession No: KCLRF-BP-00416) producing the antibody specifically binding to the bPAG1 or the antigen-binding fragment thereof. Details of the antibody specifically binding to the bPAG1 or the antigen-binding fragment thereof are the same as described above. In detail, in one embodiment of the present disclosure, spleen cells of a mouse were harvested and fused with myeloma cells of a mouse. After the fused cells were cultured, only hybridoma cells in which an antibody specifically binding to the bPAG1 which is a bovine gestational plasma was identified were selected. Afterwards, the selected hybridoma cell was deposited with the Korean Cell Line Research Foundation (KCLRF) and assigned Accession No: KCLRF-BP-00416 on Dec. 22, 2017. The address of the KCLRF is Cancer Research Institute, Seoul National University College of Medicine, 103 Daehak-ro, Chongno-gu, Seoul 110-799, KOREA.

The hybridoma cell producing the antibody may be used to culture the antibody in a large quantity in vitro or in vivo. The antibody produced by the hybridoma cell may be used without purification. However, in order to obtain the best results, the antibody may be highly purified for use at a purity of, for example, 95% or more, according to a known method. The antibody may be separated from a culture medium or an ascite fluid by using a purification method, such as dialysis, salt precipitation, chromatography, and the like.

According to another aspect of the present disclosure, provided is a composition for diagnosis of bovine pregnancy, the composition including the antibody specifically binding to the bPAG1 or the antigen-binding fragment thereof. Details of the antibody specifically binding to bPAG1 or the antigen-binding fragment thereof are the same as described above. The composition may include a carrier for the antibody, such as a diluent, a buffer, a stabilizer, and the like. The composition may include a detection reagent for detecting an antigen-antibody complex.

According to another aspect of the present disclosure, provided is a kit for diagnosis of bovine pregnancy, the kit including the composition including an antibody specifically binding to bPAG1 or the antigen-binding fragment thereof. Details of the antibody specifically binding to the bPAG1 or the antigen-binding fragment thereof are the same as described above. In detail, the kit for diagnosis of bovine pregnancy according to the present disclosure may include, in addition to the antibody specifically binding to the bPAG1 or the antigen-binding fragment thereof, a tool or reagent used for immunological analysis. The antibody may specifically bind to the epitope polypeptide having the amino acid sequence of SEQ ID NO: 1. Here, examples of the tool or reagent used for immunological analysis are a suitable carrier, a labeling substance capable of generating a detectable signal, a solvent, a cleaning agent, and the like. When the labeling substance is an enzyme, the kit may include a substrate capable of measuring enzyme activity, a reaction stopping reagent, and the like.

The carrier may be a soluble carrier, for example, a physiologically acceptable buffer known in the art, such as PBS, an insoluble carrier, such as polystyrene, polyethylene, polypropylene, polyester, and polyacrylonitrile, a fluorine resin, cross-linked dextran, polysaccharide, a polymer such as magnetic fine particles plated with metal on latex, other paper, glass, metal, agarose, and any combination thereof.

According to another aspect of the present disclosure, provided is a method of diagnosing bovine pregnancy, the method including: contacting a sample with the antibody specifically binding to the bPAG1 or the antigen-binding fragment thereof; and detecting the bPAG1 bound by the antibody or the antigen-binding fragment thereof. Details of the antibody specifically binding to the bPAG1 or the antigen-binding fragment thereof are the same as described above.

The method of diagnosing bovine pregnancy according to an embodiment includes the contacting of the sample with the antibody specifically binding to bovine pregnancy or an antigen-binding fragment thereof. The sample may be a biological sample separated from a bovine. In detail, the sample may be milk, tissue, cells, blood, serum, plasma, saliva, or urine of a bovine to be tested for pregnancy. The contacting may include incubating the sample with the antibody or the antigen-binding fragment thereof in a liquid medium. The incubating may be performed under suitable temperature, pH, and stirring conditions for antigen-antibody binding between the antigen and the antibody in the sample. The incubating may be performed at a temperature in a range of about 2° C. to about 37° C. The incubating may be performed at a pH in a range of about 6 to about 8.

The method of diagnosing bovine pregnancy according to an embodiment includes the detecting of the antibody or the antigen-binding complex. The detecting may be performed by directly separating the antigen-antibody complex to confirm the presence thereof, or by a method, such as biochemical or immunochemical analysis, after separating the complex or without separating the complex. Such an analysis method may include a method selected from enzyme-linked immunosorbent assay (ELISA), Western blotting, immunofluorescence, immunohistochemistry staining, flow cytometry, immunocytochemistry, radioimmunoassay (RIA), immunoprecipitation assay, immunodiffusion assay, complement fixation assay, and protein chip.

Regarding the analysis methods, the antigen-antibody complex may be labeled with a detectable label or a substance capable of generating a detectable level. The detectable label or the substance capable of generating a detectable label may be selected from an enzyme, a fluorescent substance, a ligand, a luminescent substance, a microparticle, a redox molecule, and a radioisotope. The enzyme may include, for example, β-glucuronidase, β-D-glucosidase, β-D-galactosidase, urease, peroxidase, alkaline phosphatase, acetylcholine esterase, glucose oxidase, hexokinase and GDPase, RNase, glucose oxidase and luciferase, phosphofructokinase, phosphoenolpyruvate carboxylase, asparate aminotransferase, phosphoenolpyruvate decarboxylase, β-lactamase, or a combination thereof. The fluorescent material may include fluorescein, isothiocyanate, rhodamine, phycoerythrin, phycocyanin, allophycocyanin, o-phthalaldehyde, fluorescamine, and the like, but is not limited thereto. The ligand may include a biotin derivative and the like. The luminescent material may include acridinium ester, luciferin, luciferase, and the like. The microparticle may include colloidal gold, colored latex, and the like, but is not limited thereto. The redox molecule may include ferrocene, a ruthenium complex compound, viologen, quinone, Ti ion, Cs ion, diimide, 1,4-benzoquinone, hydroquinone, $K_4W(CN)_8$, $[Os(bpy)_3]^{2+}$, $[RU(bpy)_3]^{2+}$, $[MO(CN)_8]^{4-}$, and the like. The radioisotope may include $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, $^{186}Re$, and the like.

As described above, the antibody specifically binding to the bPAG1 or the antigen-binding fragment thereof specifically binds to a plasma protein that appears or increases depending on bovine pregnancy, so as to form the antigen-antibody complex. By performing analysis on the antigen-antibody complex, whether or not a bovine is pregnant may be diagnosed by a relatively simple method, thereby increasing the reproduction efficiency of bovines so that the antibody or the antigen-binding fragment thereof may be usefully used in the livestock industry.

An aspect relates to an antibody specifically binding to bovine pregnancy-associated glycoprotein 1 (bPAG1) or an antigen-binding fragment thereof. Since the antibody specifically binds to bPAG1 which is a bovine gestational plasma protein, it is possible to easily diagnose pregnancy in animals of which reproduction is important, such as bovines, and thus the antibody or the antigen-binding fragment thereof may be usefully used in the livestock industry by increasing the reproduction efficiency.

BRIEF DESCRIPTION OF DRAWINGS

FIG. 1 shows the bovine pregnancy-associated glycoprotein 1 (bPAG1) entire amino acid sequence of SEQ ID NO: 7. In FIG. 1, bold letters indicate an amino acid sequence of SEQ ID NO: 1 to which an antibody or antigen-binding fragment according to the present invention specifically binds.

FIG. 3 shows the results confirmed by Bradford assay after separating immunoglobulin M. In FIG. 3.

DETAILED DESCRIPTION OF EMBODIMENTS

Figure 2:
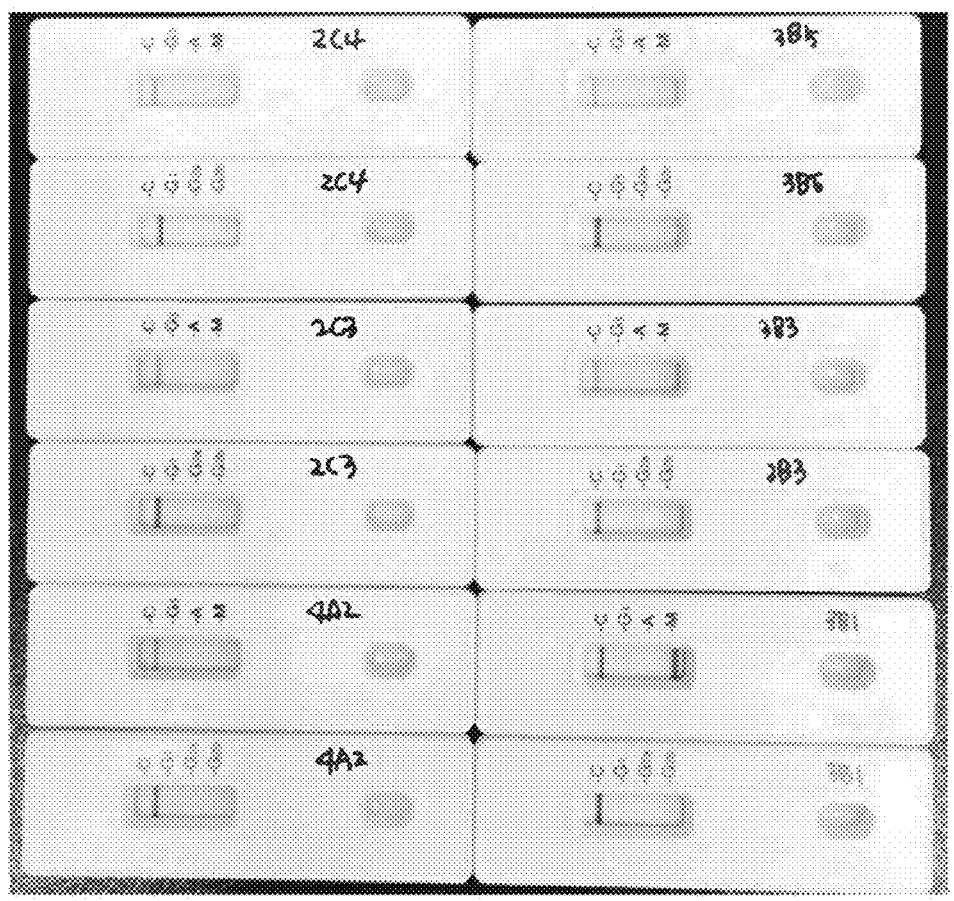
FIG. 2 shows the results of the isotype screening test.

Hereinafter, to promote understanding of the present disclosure, preferable Examples are provided. However, Examples below are only provided to more easily understand the present disclosure more easily, and the contents of the present disclosure are not limited by Examples below.

Preparation Example

As an antigen peptide for preparing an antibody, 40 amino acid sequences were selected from the 150$^{th}$ to the 200$^{th}$ amino acid sequences and the 350$^{th}$ to the 400$^{th}$ amino acid sequences of bovine pregnancy-associated glycoprotein 1 (bPAG1). Four types of the antigen peptide were used depending on the presence of Keyhole limpet hemocyanin (KLH). The amino acid sequence of the bPAG1 fragment may include sequences of SEQ ID NO: 5 (PAG1_100) and SEQ ID NO: 6 (PAG1_300).

EXAMPLES

Example 1. Induction of Immune Response Using Antigen 1-1. bPAG1_100

100 µl of the antigen (bPAG1_100) of Preparation Example and a complete adjuvant of the same amount were used to prepare an antigen emulsion. Then, an 8-week-old female mouse (BALB/C) was administered subcutaneously with the antigen emulsion, so as to induce an immune response. After the first administration, the mouse was administered subcutaneously with 100 µl of the same antigen and an incomplete adjuvant of the same amount every two weeks. Matters to consider regarding the antigen administration schedule or the like are shown in Table 1 below.

1-2. bPAG1_100-KLH

The same process as Example 1-1 was performed, except that the bPAG1_100-KLH antigen was used.

1-3. bPAG1_300

The same process as Example 1-1 was performed, except that the bPAG1_300 antigen was used.

1-4. bPAG1_300-KLH

The same process as Example 1-1 was performed, except that the bPAG1_300-KLH was used.

TABLE 1

| Order | Antigen | Concentration (mg/ml) | Dose (µg) | |
|---|---|---|---|---|
| First | Example 1-1 | 0.5 | 75 | +Complete adjuvant |
| First | Example 1-2 | 0.3125 | 46.875 | (v/v 1:1 mixture) |
| Second | Example 1-1 | 0.5 | 75 | +Incomplete adjuvant |
| Second | Example 1-2 | 0.3125 | 46.875 | (v/v 1:1 mixture) |
| First | Example 1-3 | 0.5 | 75 | +Complete adjuvant |
| First | Example 1-4 | 0.3125 | 46.875 | (v/v 1:1 mixture) |
| Third | Example 1-1 | 0.5 | 75 | +Complete adjuvant |
| Third | Example 1-2 | 0.3125 | 46.875 | (v/v 1:1 mixture) |
| Second | Example 1-3 | 0.5 | 75 | +Incomplete adjuvant |
| Second | Example 1-4 | 0.3125 | 46.875 | (v/v 1:1 mixture) |
| Third | Example 1-3 | 0.5 | 75 | +Complete adjuvant |
| Third | Example 1-4 | 0.3125 | 46.875 | (v/v 1:1 mixture) |

Example 2. Confirmation of Antibody Titer 2-1. bPAG1_100

After the antigen administration of Example 1-1 was performed three times, a small amount of serum was collected from the tail vein of the mouse, so as to confirm the titer of polyclonal antibodies in the serum through ELISA. In detail, a reaction was allowed at a temperature of 4° C. for 18 hours by using 100 µl of the PAG1_100 antigen (2 µg/ml) per well, and a coating process was performed thereon. On the following day, a reaction blocking process was performed thereon at room temperature for 1 hour by using a blocking buffer. Afterwards, the serum collected from the mouse blood was diluted according to a magnification ratio, and 100 µl of the diluted serum was dispensed into each well for a reaction at room temperature for 1 hour. The well plate where the reaction was completed was washed with PBST, and goat anti-mouse IgG-HRP in which HRP was conjugated was diluted at a ratio of 1:2,000, and 100 µl of the diluted goat anti-mouse IgG-HRP was dispensed into each well for a reaction at room temperature for 1 hour. Afterwards, the well plate was washed again with PBST, and a TMB solution was dispensed thereinto for a reaction for 15 minutes. Then, a reaction stopping solution was used to terminate the reaction. Titers in the serum were confirmed by measuring absorbance values at 450/620 nm, and the results are shown in Tables 2 and 3 below.

2-2. bPAG1_100-KLH

The same process as Example 2-1 was performed, except that the bPAG1_100-KLH antigen was used.

2-3. bPAG1_300

The same process as Example 2-1 was performed, except that the bPAG1_300 antigen was used.

2-4. bPAG1_300-KLH

The same process as Example 2-1 was performed, except that the bPAG1_300-KLH antigen was used.

extracted spleen and placed on a 60 mm dish containing the DMEM to be separated as single cells. Afterwards, the red blood cells mixed in the lymphocytes were removed by using an RBC lysis buffer, and washed with fresh DMEM. Then, prepared myeloma cells (SP2/0 Ag 14—ATCC #CRL-1581) and the treated lymphocytes were hybridized at a ratio of 1:5 based on the number of the myeloma cells. Then, 1.7 ml of PEG1500 was added to the hybridized cells (i.e., hybridoma cells) to induce cell fusion, and 200 μl of the resulting hybridoma cells was dispensed into each well of a 96-well plate for incubation in a $CO_2$ incubator. After 2 days of the cell fusion, 50% of each well was replaced with hypoxanthine-aminopterinthymidine (HAT) medium. After 12 days of the cell fusion, the production of colonies was confirmed to determine whether or not the cells reacted with a bPAG1 peptide (i.e., an antigen to be confirmed by ELISA) in the same manner as ELISA (Asb. 450 nm) of Example 2.

TABLE 2

PAG1-100 coating

| Serum concentration | | Control | NC1 | NC2 | NC3 | Example 2-1 | Example 2-2 | Example 2-3 | Example 2-4 |
|---|---|---|---|---|---|---|---|---|---|
| ×100 | A | 0.203 | 0.087 | 0.145 | 0.111 | 2.393 | 2.483 | 0.195 | 0.151 |
| ×200 | B | 0.084 | 0.037 | 0.062 | 0.045 | 2.176 | 2.265 | 0.087 | 0.069 |
| ×400 | C | 0.03 | 0.014 | 0.025 | 0.018 | 2.018 | 1.916 | 0.035 | 0.029 |
| ×800 | D | 0.013 | 0.009 | 0.011 | 0.01 | 1.547 | 1.518 | 0.015 | 0.013 |
| ×1600 | E | 0.009 | 0.006 | 0.008 | 0.006 | 1.029 | 0.998 | 0.016 | 0.019 |
| ×3200 | F | 0.006 | 0.006 | 0.006 | 0.007 | 0.562 | 0.554 | 0.014 | 0.002 |
| ×6400 | G | 0.005 | 0.005 | 0.011 | 0.011 | 0.288 | 0.263 | 0.005 | 0.005 |
| ×12800 | H | 0.005 | 0.005 | 0.005 | 0.005 | 0.134 | 0.127 | 0.005 | 0.005 |

TABLE 3

PAG1-300 coating

| Serum concentration | | Control | NC1 | NC2 | NC3 | Example 2-1 | Example 2-2 | Example 2-3 | Example 2-4 |
|---|---|---|---|---|---|---|---|---|---|
| ×100 | A | 0.15 | 0.075 | 0.125 | 0.082 | 0.159 | 0.012 | 2.558 | 2.583 |
| ×200 | B | 0.059 | 0.027 | 0.048 | 0.033 | 0.073 | 0.048 | 2.317 | 2.34 |
| ×400 | C | 0.021 | 0.012 | 0.018 | 0.015 | 0.03 | 0.019 | 2.114 | 2.164 |
| ×800 | D | 0.01 | 0.007 | 0.009 | 0.008 | 0.013 | 0.01 | 1.828 | 1.921 |
| ×1600 | E | 0.007 | 0.006 | 0.006 | 0.007 | 0.007 | 0.005 | 1.434 | 1.446 |
| ×3200 | F | 0.005 | 0.005 | 0.006 | 0.005 | 0.006 | 0.006 | 0.869 | 0.887 |
| ×6400 | G | 0.005 | 0.004 | 0.005 | 0.005 | 0.005 | 0.004 | 0.385 | 0.454 |
| ×12800 | H | 0.005 | 0.004 | 0.005 | 0.005 | 0.005 | 0.005 | 0.224 | 0.246 |

As a result, as shown in Tables 2 and 3, it was confirmed through the analysis of antigenicity of the bPAG1 that the synthesized PAG1-100 peptide and the synthesized PAG1-300 peptide mass-produced antibodies against the bPAG1.

Example 3. Preparation of Hybridoma Cell Producing Monoclonal Antibody Against bPAG1 and Separation of Monoclonal Antibody 3-1. Preparation of Hybridoma Cell Once the production of antibodies, which have high titers based on the titers in the mouse serum confirmed by the antibody titer confirmation test of Example 2, was confirmed, lymphocytes of the mouse were separated and subjected to cell fusion. In detail, the spleen of the mouse in which the immune response was introduced in Examples 1-1 to 1-4 was extracted without damage, washed with Dulbecco/Vogt modified Eagle's minimal essential medium (DMEM). Then, lymphocytes were separated from the Referring to the ELISA results, when the hybridoma cells had the O.D value of 1.0 or more, the hybridoma cells were regarded as positive cells and selected as parent cells for producing monoclonal antibodies. The results are shown in Table 4 below.

TABLE 4

| bPAG100 | | | | | | bPAG300 |
|---|---|---|---|---|---|---|
| 1A1 | 1B3 | 2A6 | 2C2 | 3A6 | N | 4A1 |
| 1.877 | 0.97 | 2.49 | 1.475 | 0.704 | 0.02 | 3.036 |
| 1A2 | 1B4 | 2B1 | 2C3 | 3B1 | | 4A2 |
| 1.689 | 1.776 | 1.797 | 1.382 | 1.558 | | 1.966 |
| 1A3 | 1B5 | 2B2 | 2C4 | 3B2 | | 4A3 |
| 2.651 | 0.251 | 0.985 | 3.283 | 2.766 | | 0.389 |
| 1A4 | 2A1 | 2B3 | 3A1 | 3B3 | | 4A4 |
| 2.146 | 2.649 | 1.11 | 1.504 | 2.996 | | 0.181 |
| 1A5 | 2A2 | 2B4 | 3A2 | 3B4 | | 4A5 |
| 0.68 | 2.631 | 0.157 | 0.478 | 1.053 | | 0.146 |
| 1A6 | 2A3 | 2B5 | 3A3 | 3B5 | | N |

TABLE 4-continued

| | bPAG100 | | | | bPAG300 |
|---|---|---|---|---|---|
| 1.431 | 3.164 | 3.106 | 0.904 | 1.058 | 0.125 |
| 1B1 | 2A4 | 2B6 | 3A4 | 3B6 | |
| 2.522 | 2.847 | 3.16 | 0.076 | 0.745 | |
| 1B2 | 2A5 | 2C1 | 3A5 | 3C1 | |
| 0.872 | 0.108 | 2.929 | 1.133 | 2.246 | |

3-2. Screening of Hybridoma Cell Line Producing Monoclonal Antibody

Cells specifically reacting only to the bPAG1 among the hybridoma cell group prepared in Example 3-1 were selected. Then, in order to confirm whether the antibodies were produced, screening was performed on the selected from cells according to enzyme immunoassay.

After 12 days of the cell fusion, the medium was replaced with fresh medium, and the original medium which is regarded as a primary antibody was subjected to ELISA. Following the ELISA, wells showing positive results for the corresponding antigen were selected and transferred to a 24-well plate for culture. A hybridoma cell line cultured in the 24-well plate was subjected again to ELISA in the same manner as described above, so as to confirm antibody titers. At the same time, the antibody-producing cell line was subjected to the second screening. The absorbance (expressed as O.D value) of the hybridoma cells grown in the 24-well plate was confirmed by ELISA. Only the hybridoma cells having the absorbance value of 1 or more were selected and transferred to a 6-well culture flask. After the hybridoma cells were cultured and centrifuged, the supernatant was obtained, confirmed by ELISA again, and subjected to the third screening. The hybridoma cells selected based on the third screening were transferred again to a 75T/C culture flask, and then cultured. The absorbance of the hybridoma cells was confirmed by ELISA, and only the hybridoma cells having the absorbance value of 1 or more were selected. The cell lines selected through the process above are shown in Table 5 below.

TABLE 5

| bPAG1_100 | 1A6, 2A6, 2B6, 2C4 |
|---|---|
| bPAG1_100-KLH | 3A6, 3B1, 3B3, 3B5 |
| bPAG1_300 | 4A1, 4A3 |

As shown in Table 5, 1A6, 2A6, 2B6, 2C4, 3A6, 3B1, 3B3, and 3B5 cell lines were finally selected for producing antibodies against bPAG1-100 as a binding site, and 4A1 and 4A3 cell lines were finally selected from for producing antibodies against bPAG-300 as a binding site. Among these cell lines, the 3B1 cell line was deposited with the KCLRF on Dec. 5, 2017 (Accession No: KCLRF-BP-00416).

Example 4. Production and Purification of Monoclonal Antibody Against bPAG1

In order to mass-produce monoclonal antibodies against the bPAG1 from the finally selected from hybridoma cells of Example 3-2, 0.5 ml of an incomplete adjuvant was administered to the abdominal cavity of a 6-week-old mouse (BALB/C). After 3 days of the administration, among the finally selected from hybridoma cells of Example 3-1, the cells confirmed to have high O.D values were each administered at 100 µl ($1\times10^6$ cells) per mouse. After 6 to 10 days of the administration, ascite was collected from the abdominal cavity of the mouse.

Example 5. Separation of Monoclonal Antibody Against bPAG1

In order to separate the antibodies specifically binding to the bPAG1 from the selected hybridoma cells of Example 3, the collected ascite was injected into a dialysis pack by using a syringe. Afterwards, 2 L of 2 mM phosphate buffer (PB) was added to a beaker, and a dialysis solution containing a magnetic bar and a sample was added thereto, followed by dialysis at 4° C. for 3 days to 4 days. Here, the buffer was replaced with fresh buffer once a day. After the dialysis was completed, the liquid present in the dialysis solution was collected and centrifuged. The supernatant was then collected therefrom to quantify proteins, and the antigen-antibody response on a membrane was also confirmed.

Figure 3A:
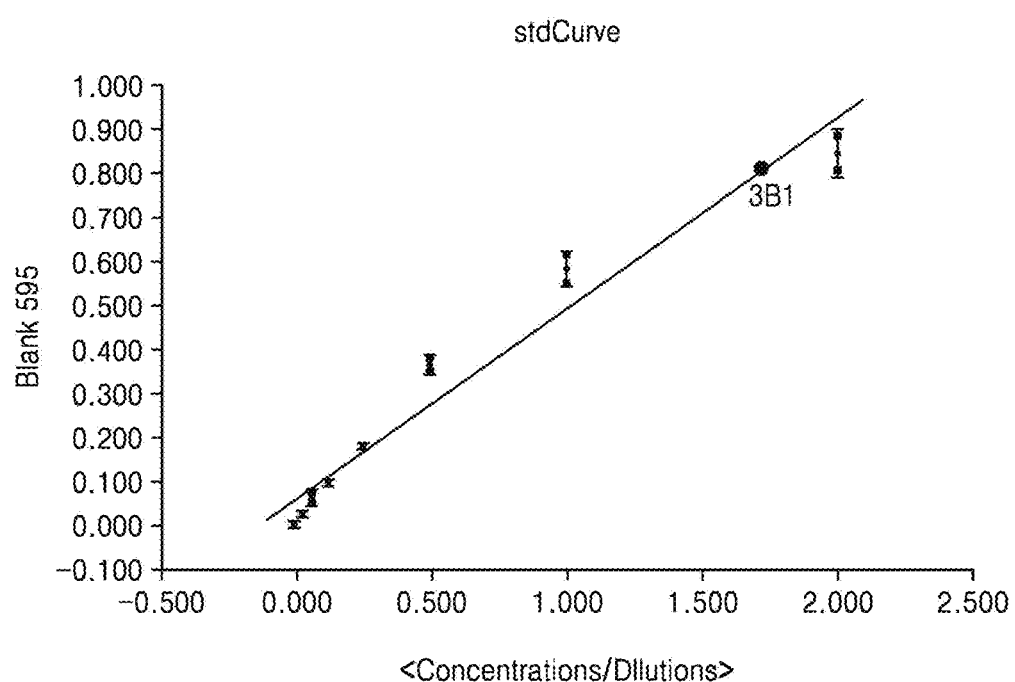
FIG. 3A shows a quantitative graph of separated 3B1 clones.
Figure 3B:
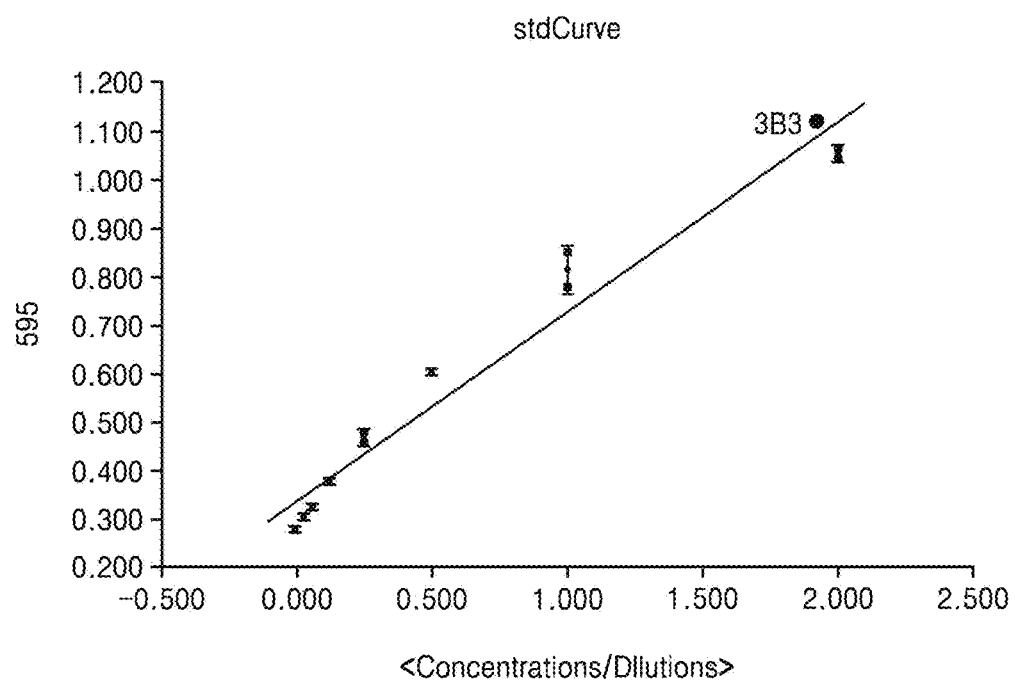
FIG. 3B shows a quantitative graph of separated 3B3 clones.
Figure 3C:
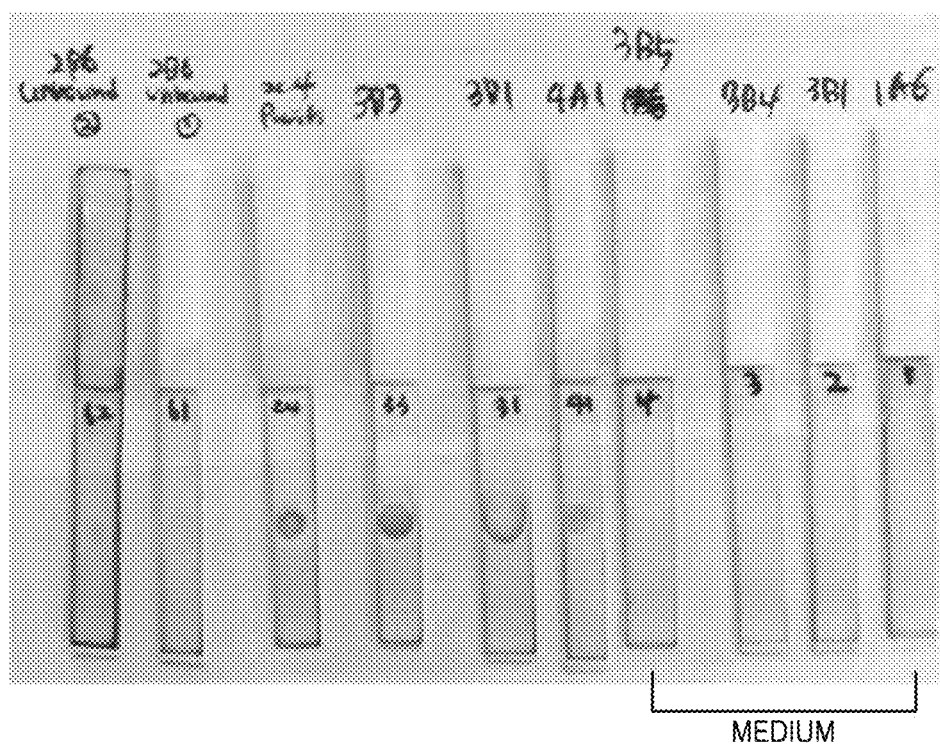
FIG. 3C is a photograph showing the degree of activity of the separated-purified antibody on a membrane.

As a result, as shown in FIGS. 3A and 3B, in the case of the 3B1 hybridoma cell line, about 1.5 mg of the antibody was produced per 1 ml of the ascite, and in the case of the 3B3 hybridoma cell line, about 2 mg of the antibody was produced per 1 ml of the ascite. In order to confirm the activity of the antibody separated from the process above on the membrane, a small amount of serum of a pregnant bovine was loaded onto the membrane. The membrane was then dried, and each antibody conjugated with a gold particle was mixed with a developing solution and flowed along the membrane. As a result, as shown in FIG. 3C, the 2C4, 3B1, 3B3, and 4A1 antibodies each showed a clear spot indicating the binding to the antigen (bPAG1).

Example 6. Analysis of Epitope for Monoclonal Antibody Against bPAG1

Epitope mapping was performed by using the peptides used in the antibody production. As the peptides used in the mapping, only some peptides, e.g., the 100-sized peptides and the 300-sized peptides, of the PAG1 protein used in the production of the existing antigen were used. As shown in Table 6 below, the mapping proceeded with four types of the peptides.

TABLE 6

| Peptide 1 | ASSDLWVPSDFCTSPACSTH | SEQ ID NO: 1 |
|---|---|---|
| Peptide 2 | CVRFRHLQSSTFRLTNKTFRI | SEQ ID NO: 2 |
| Peptide 3 | GAIPRGSEHYVPCSEVNTLP | SEQ ID NO: 3 |
| Peptide 4 | CSIVFTINGINYPVPGRAYIL | SEQ ID NO: 4 |

In detail, each of the antigen bPAG1_100 and the antigen bPAG1_300 was dispensed at 25 µl, 50 µl, 100 µl, and 200 µl per well, and a coating process was performed thereon. Then, a reaction was allowed at room temperature for 2 hours. Afterwards, a blocking process was performed thereon at room temperature for 1 hour by using a blocking buffer, and the purified sample was dispensed at 100 µl per well. Then, a reaction was allowed at room temperature for 1 hour. Next, the well plate where the reaction was completed was washed with PBST, and goat anti-mouse IgM conjugated with HRP was diluted at a ratio of 1:50,000 and dispensed into each well at 100 µl per well. Then, a reaction was allowed for 1 hour. After the reaction was completed, the well plate was washed again with PBST, and a TMB solution was dispensed thereinto for a reaction for 15 minutes. Then, a reaction stopping solution was used to terminate the reaction, and the absorbance values at 450/620 nm were measured, so as to confirm the antibody titers in the sample.

Figure 4:
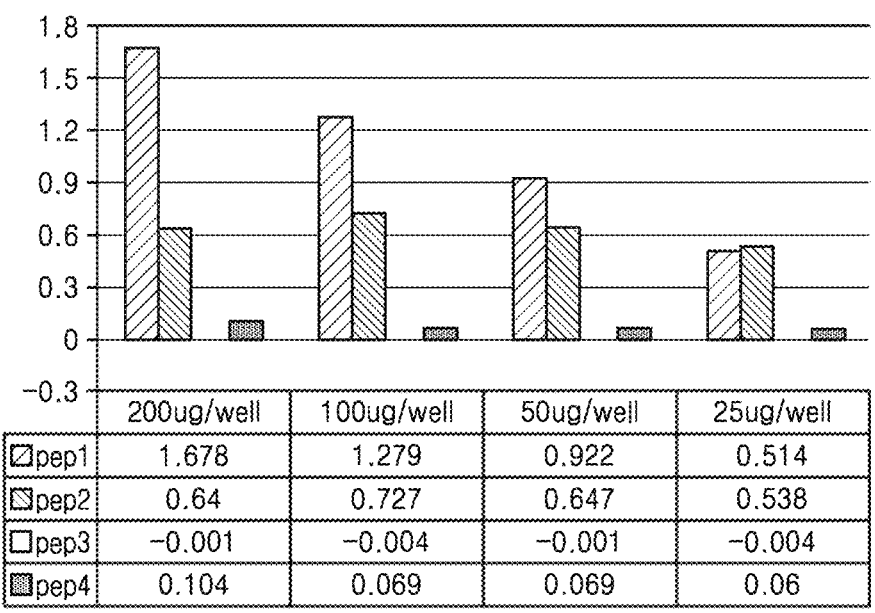
FIG. 4 shows the analysis results of epitope for a monoclonal antibody against the bPAG1.
Figure 5:
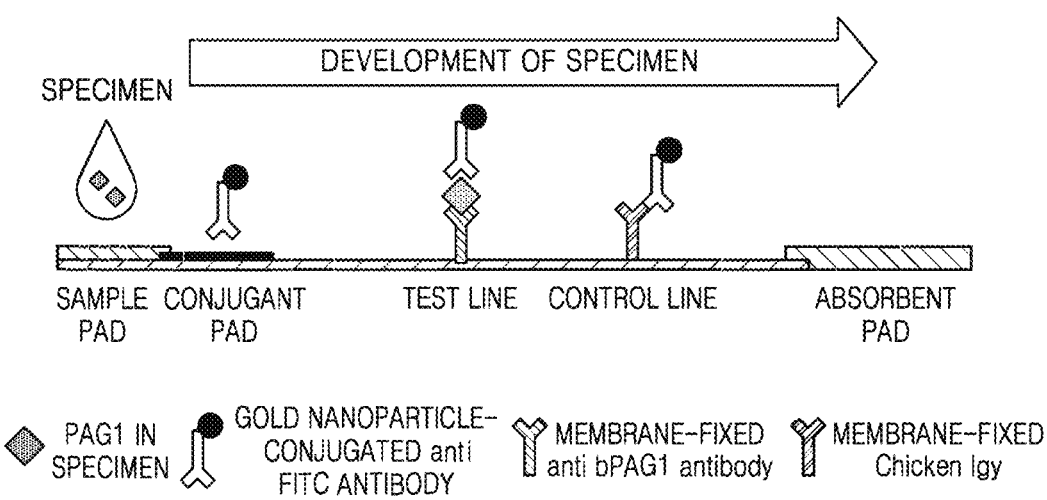
FIG. 5 is a schematic diagram showing a method of diagnosing bovine pregnancy.

As a result, as shown in FIG. 4, it was confirmed that the amount of the antibody specifically binding to the antigen increased depending on the concentration of the antigen. In particular, in the case of Peptide 1, the amount of Peptide 1 specifically binding to the antigen was remarkably high compared to the amounts of Peptides 2 to 4 at the same concentration of the antigen, and accordingly, it was confirmed that Peptide 1 had the amino acid sequence of the epitope for the antibody of the present disclosure.

Example 7. Diagnosis of Bovine Pregnancy by Using Separated and Purified Antibody By using the antibody selected in Example 3, the bPAG1 which is known to be present in the blood of pregnant bovines was detected. In detail, the antibody was dispensed into a membrane, and an antibody with an antigen-binding site, which is different from the antibody of the present disclosure, to which gold particles are bound was used for artificial insemination. Then, the blood was collected from a 6 weeks-old bovine, a 7 weeks-old bovine, and a 8 weeks-old bovine, and then centrifuged to separate serum. 0.05 ml of the separated serum was loaded onto a sample-loading section of a simplified kit, and after 15 minutes, the results were decided.

Figure 6:
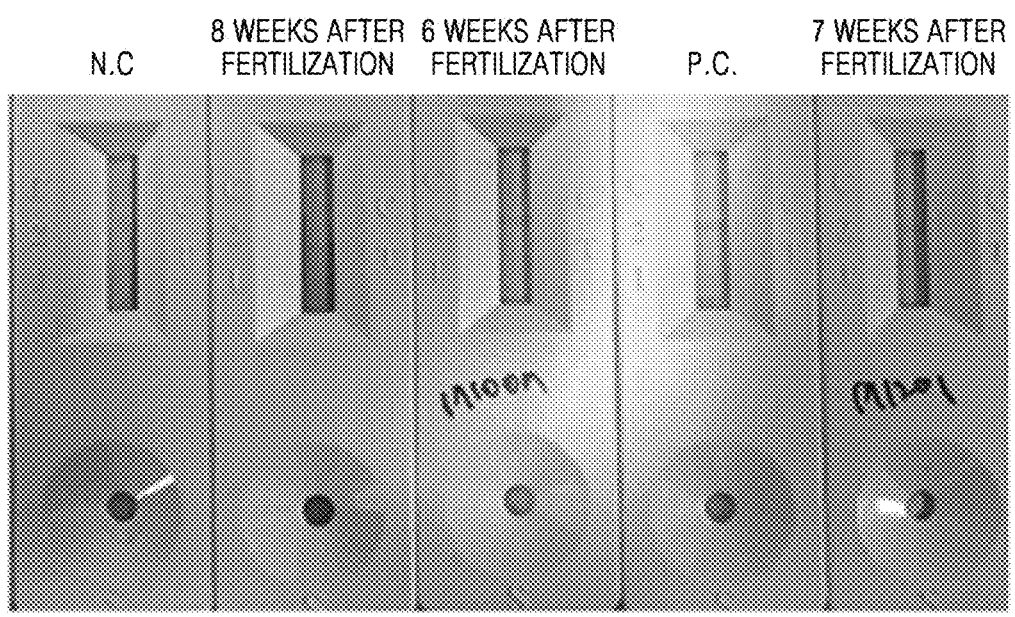
FIG. 6 is a photograph showing the results of diagnosis of bovine pregnancy by using a simplified kit.

As a result, as shown in FIG. 6, it was confirmed that a band was produced on an inspection line after 6 weeks of the fertilization. That is, the bovine pregnancy was able to be diagnosed by confirming the presence of the bPAG1 in the bovine blood by using the antibody.

The invention claimed is:

1. An antibody specifically binding to bovine pregnancy-associated glycoprotein 1 (bPAG1) or an antigen-binding fragment thereof,
   wherein the antibody or the antigen-binding fragment thereof is produced by the hybridoma cell line identified by Accession No: KCLRF-BP-00416.

2. The hybridoma cell line identified by Accession No: KCLRF-BP-00416 producing an antibody specifically binding to bovine pregnancy-associated glycoprotein 1 (bPAG1) or an antigen-binding fragment thereof.

3. A composition for diagnosis of bovine pregnancy, the composition comprising the antibody of claim 1.

4. A kit for diagnosis of bovine pregnancy, the kit comprising the antibody of claim 1.

5. A method of diagnosis of bovine pregnancy, the method comprising:
   contacting a sample with an antibody or an antigen-binding fragment thereof; and
   detecting the bPAG1 bound by the antibody or the antigen-binding fragment thereof,
   wherein the antibody or the antigen-binding fragment thereof is produced by the hybridoma cell line identified by Accession No: KCLRF-BP-00416.

6. The method of claim 5, wherein the detecting the bPAG1 is performed by an analysis method selected from enzyme-linked immunosorbent assay (ELISA), Western blotting, immunofluorescence, immunohistochemistry staining, flow cytometry, immunocytochemistry, radioimmunoassay (RIA), immunoprecipitation assay, immunodiffusion assay, complement fixation assay, and protein chip.

* * * * *